(12) United States Patent
Kah, Jr.

(10) Patent No.: US 10,215,676 B2
(45) Date of Patent: Feb. 26, 2019

(54) PLANT STEM TREE BRANCH OR TRUNK MOISTURE PROBE

(71) Applicant: Carl L. C. Kah, Jr., North Palm Beach, FL (US)

(72) Inventor: Carl L. C. Kah, Jr., North Palm Beach, FL (US)

( * ) Notice: Subject to any disclaimer, the term of this patent is extended or adjusted under 35 U.S.C. 154(b) by 0 days.

(21) Appl. No.: 13/657,317

(22) Filed: Oct. 22, 2012

(65) Prior Publication Data

US 2014/0109658 A1 Apr. 24, 2014

(51) Int. Cl.
*G01N 5/02* (2006.01)
*G01N 33/00* (2006.01)
*G01N 27/22* (2006.01)

(52) U.S. Cl.
CPC ............. *G01N 5/025* (2013.01); *G01N 5/02* (2013.01); *G01N 33/0098* (2013.01); *G01N 27/223* (2013.01)

(58) Field of Classification Search
CPC ........ G01N 5/02; G01N 19/10; G01N 27/048; G01N 27/223; G01N 5/025; G01N 33/00; G01N 33/246
USPC ............. 73/73; 137/78.3; 324/694, 689, 696
See application file for complete search history.

(56) References Cited

U.S. PATENT DOCUMENTS

| | | | | |
|---|---|---|---|---|
| 3,807,055 A * | 4/1974 | Kraxberger | ............. | F26B 25/22 324/605 |
| 3,967,198 A * | 6/1976 | Gensler | ............. | 324/72 |
| 4,259,633 A * | 3/1981 | Rosenau | ............. | G01R 27/02 324/694 |
| 4,380,169 A * | 4/1983 | Graham | ............. | 73/73 |
| 4,638,594 A * | 1/1987 | Huguet | ............. | A01G 25/16 47/1.01 R |
| 4,745,805 A * | 5/1988 | Granier | ............. | G01N 33/0098 47/1.01 R |
| 4,817,427 A * | 4/1989 | Kitano | ............. | G01F 1/6847 47/1.01 R |
| 5,224,769 A * | 7/1993 | Holbrook | ............. | G01N 27/223 324/664 |
| 5,269,183 A * | 12/1993 | Van Bavel | ............. | G01F 1/68 73/204.22 |
| 5,341,673 A * | 8/1994 | Burns et al. | ............. | 73/73 |
| 5,367,905 A * | 11/1994 | Senock | ............. | G01F 1/6847 73/204.22 |
| 5,859,536 A * | 1/1999 | Stockton | ............. | G01R 27/2623 239/64 |
| 6,185,833 B1 * | 2/2001 | Bravdo | ............. | G01B 7/06 33/783 |
| 6,577,143 B2 * | 6/2003 | Arsenault | ............. | G01N 27/048 324/689 |
| 6,708,555 B1 * | 3/2004 | Lyons, Jr. | ............. | G01N 27/223 324/640 |
| 6,870,376 B1 * | 3/2005 | Gensler | ............. | 324/664 |
| 7,688,215 B2 * | 3/2010 | Vokey | ............. | G01M 3/16 340/601 |

(Continued)

*Primary Examiner* — Son Le
*Assistant Examiner* — Marrit Eyassu
(74) *Attorney, Agent, or Firm* — Amster, Rothstein & Ebenstein LLP

(57) ABSTRACT

A moisture probe or sensor including an attachment element configured for attachment to a plant, bush or tree to determine a moisture content of the plant bush or tree. The moisture probe including a transceiver configured to transmit a moisture signal indicative of the moisture content of the plant, tree or plant.

12 Claims, 5 Drawing Sheets

(56) References Cited

U.S. PATENT DOCUMENTS

| | | | |
|---|---|---|---|
| 8,228,504 B2* | 7/2012 | Galtie | A01G 7/00 356/432 |
| 2007/0157512 A1* | 7/2007 | Wein et al. | 47/48.5 |
| 2008/0211521 A1* | 9/2008 | Lock | G01N 27/048 324/696 |
| 2009/0177330 A1* | 7/2009 | Kah, Jr. | 700/284 |
| 2010/0182604 A1* | 7/2010 | Galtie | A01G 7/00 356/432 |
| 2010/0251807 A1* | 10/2010 | Morton | 73/73 |

* cited by examiner

PLANT STEM TREE BRANCH OR TRUNK MOISTURE PROBE

CROSS REFERENCE TO RELATED APPLICATIONS

The present application claims benefit of and priority to U.S. Provisional Patent Application Ser. No. 61/550,014 entitled PLANT STEM TREE BRANCH OR TRUNK MOISTURE PROBE, filed Oct. 21, 2011, the entire content of which is hereby incorporated by reference herein.

The present application is also related to U.S. patent application Ser. No. 12/340,427 entitled WIRELESS MOISTURE PROBE, RECEIVING CONTROLLER AND IRRIGATION CONTROL SYSTEM, filed Dec. 19, 2008, the entire contents of which are hereby incorporated by reference herein.

BACKGROUND

Field of the Disclosure

The present disclosure relates to a method and apparatus for detecting the moisture level in plants, bushes or trees to allow for assessing the health of the plant and for control of a watering cycle for the plant.

Related Art

U.S. patent application Ser. No. 12/340,427 relates to weather and moisture sensing control of irrigation systems watering programs. A remotely located periodically transmitting moisture sensing probe is discussed for total control of the in soil, root zone water replacement need of plant material.

Monitoring the water content in the soil, however, may not provide an accurate measure of the amount of water that is actually absorbed by the plant or tree. Further, monitoring the water content in the soil alone does not provide sufficient information to determine the health of the plant, tree or bush. The plant may already be dead, so that additional watering of the soil would provide no benefit.

Accordingly, it would be desirable to provide a moisture probe or sensor that provides moisture information directly from the plant itself related directly to the plant or tree.

SUMMARY

It is an object of the present disclosure to provide a moisture probe or sensor that provides a moisture level in a plant, bush or tree to allow assessment of the health of the plant, bush or tree and for control of a watering cycle thereof.

An objective of the disclosure is to provide a simple moisture probe or sensor configuration, which may easily be attached to a plant, bush or tree to determine a relative moisture reading thereof.

Another object is for the moisture probe to utilize the measurement of the change in dielectric constant of the plant material as an indicator of the percentage by volume of the moisture content in the plant material where the probe has been attached.

Another object of the present disclosure is to provide a probe or sensor that is self-powered and capable of periodically transmitting a signal identifying itself and the relative change in the dielectric constant of the plant material which can be used to determine relative moisture change in the plant material.

A moisture probe in accordance with an embodiment of the present application includes an attachment element configured for attachment to the plant, at least one electrode, positioned on the attachment element and structured for contact with the plant, measurement circuitry connected to the electrode and operable to provide a measurement signal indicative of the moisture content in the plant, and a transceiver operable to periodically transmit the measurement signal.

A method of sensing moisture in a plant in accordance with an embodiment of the present disclosure includes providing a moisture probe configured for attachment to the plant, attaching the moisture probe to the plant such that at least one electrode of the moisture probe is positioned inside the plant, sensing, using the at least one electrode, a dielectric constant of the plant material and determining the moisture content of the plant based on the dielectric constant of the plant material.

Other features and advantages of the present invention will become apparent from the following description of the invention which refers to the accompanying drawings.

DETAILED DESCRIPTION OF EMBODIMENTS OF THE INVENTION

Figure 1:
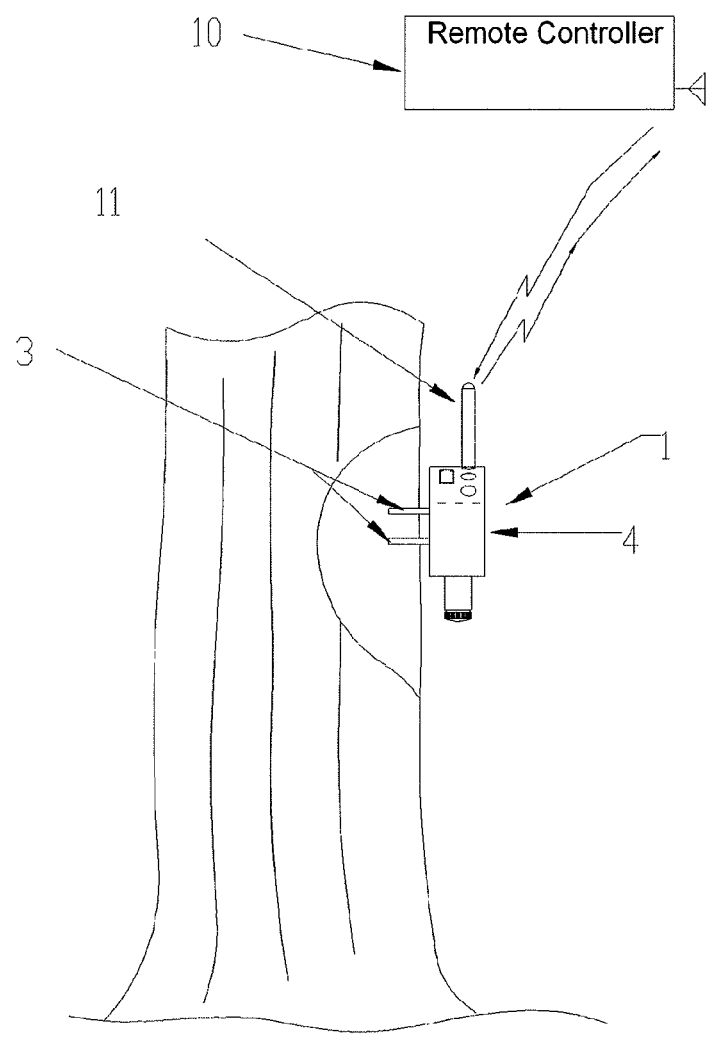
FIG. 1 illustrates a moisture probe connected to a tree in accordance with an embodiment of the present application.

A moisture probe or sensor 1 in accordance with an embodiment of the present disclosure is illustrated in FIG. 1. The moisture probe or sensor 1 provides a simple method of providing for the moisture needs of a plant, bush or tree by sensing the moisture level in the stem, trunk or limbs thereof and then controlling watering needs of the plant by monitoring the moisture level in the plant material itself rather than with a weather station or in-soil moisture probe. This information is preferably periodically transmitted to a remote irrigation controller 10, which may use this information to modify, or simply confirm, that an irrigation program is providing sufficient moisture to the plant, bush or tree. In a preferred embodiment, the transmission of the moisture information is wireless, however, if desired, a wired connection to irrigation controller 10 could be used. The controller 10 may be similar to that described in U.S. patent application Ser. No. 12/340,427, which has been incorporated by reference herein.

One benefit of monitoring moisture in the plant, bush or tree itself is that it is somewhat easier to clip or attach a moisture probe to the stem, branch or trunk of a plant, bush or tree than it is to put a moisture probe into the ground in the root zone of the plant or tree.

In addition, if the health of the plant, bush or tree is not good, or the plant material has already been damaged for lack of water at an earlier time and passed through permanent wilt, this can be sensed by sensing the moisture content of a limb or stem of the plant. In this case, no modification of watering would be beneficial to the already damaged plant. Monitoring soil water content, however, does not provide sufficient information to determine the health of the plant, bush or tree.

The moisture content of a stem, trunk or branch that is above ground may be used to determine the relative health of the plant and to control the amount of moisture that must be added to the soil where the plant has its root zone to maintain the moisture within the plants limb, stem or trunk at an acceptable level.

Figure 2:
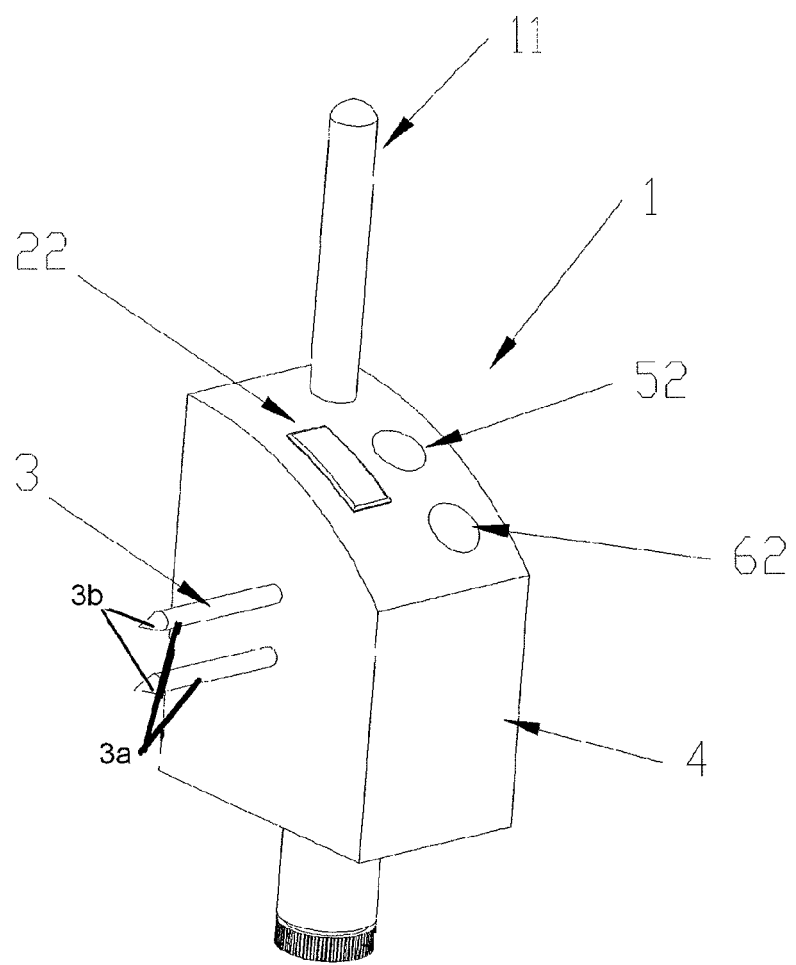
FIG. 2 is a more detailed view of the moisture probe of FIG. 1.

In FIG. 1, the moisture probe or sensor 1 includes a substantially rectangular body 4, however, any suitable shape may be used. Indeed, as is illustrated in FIG. 2, the body 4 of the probe 1 preferably includes a somewhat sloped top surface 4a. This sloped surface 4a preferably includes a transmit button 52 which may be actuated to manually transmit moisture information to the controller 10 and a reception indicator 62, which may be activated in order to confirm receipt of moisture information at the remote irrigation controller. A photocell 22 may also be provided to aid in powering the probe 1.

An attachment element 3 is provided on the probe 1 and configured to allow the probe 1 to be attached to a plant, tree or bush. The attachment element 3 is preferably provided on the body 4. Two electrodes 3a preferably extend outward from the body 4, preferably as a part of the attachment element 3. That is, the electrodes 3a are preferably incorporated into or are mounted on attachment element 3. The electrodes 3a and/or attachment element 3 may be made of a hard and durable material suitable to penetrate the trunk of a tree, or stem of a plant is indicated in FIG. 1. The electrodes 3a or attachment element 3 may have a pointed end 3b (See FIG. 2) such that insertion into a tree trunk or plant stem is easier. The electrodes 3a themselves are preferably made of an electrically conductive material.

One method of determining the moisture content of material is to measure changes in the dielectric constant of the medium being measured. The dielectric constant of water is approximately 80, the dielectric constant of minerals and organic matter such as woody tree material or plant material around 4 and the dielectric constant of air is 1. Thus, changes in water content of a particular medium will result in large changes in the dielectric constant of the medium, which can be readily measured by the probe 1.

Moisture sensing technology suitable for use with the moisture probe 1 is known in the industry and is very reliable when properly executed. In a preferred embodiment, the electrodes 3a are insulated from the plant, bush or tree material to avoid sensing the ionization of nutrients such as phosphate and nitrogen compounds and salts. Such ionized particles may cause substantial problems resulting in confusing moisture level readings.

A typical electrical circuit for the moisture probe 1 generally includes two insulated electrodes 3a. Water is a polar molecule, and thus, changes the dielectric characteristics of the soil that surrounds it. As a result, the plant, bush or tree matter around the electrodes 3a causes the electrodes to have a different capacitive impedance for different moisture levels.

Figure 3:
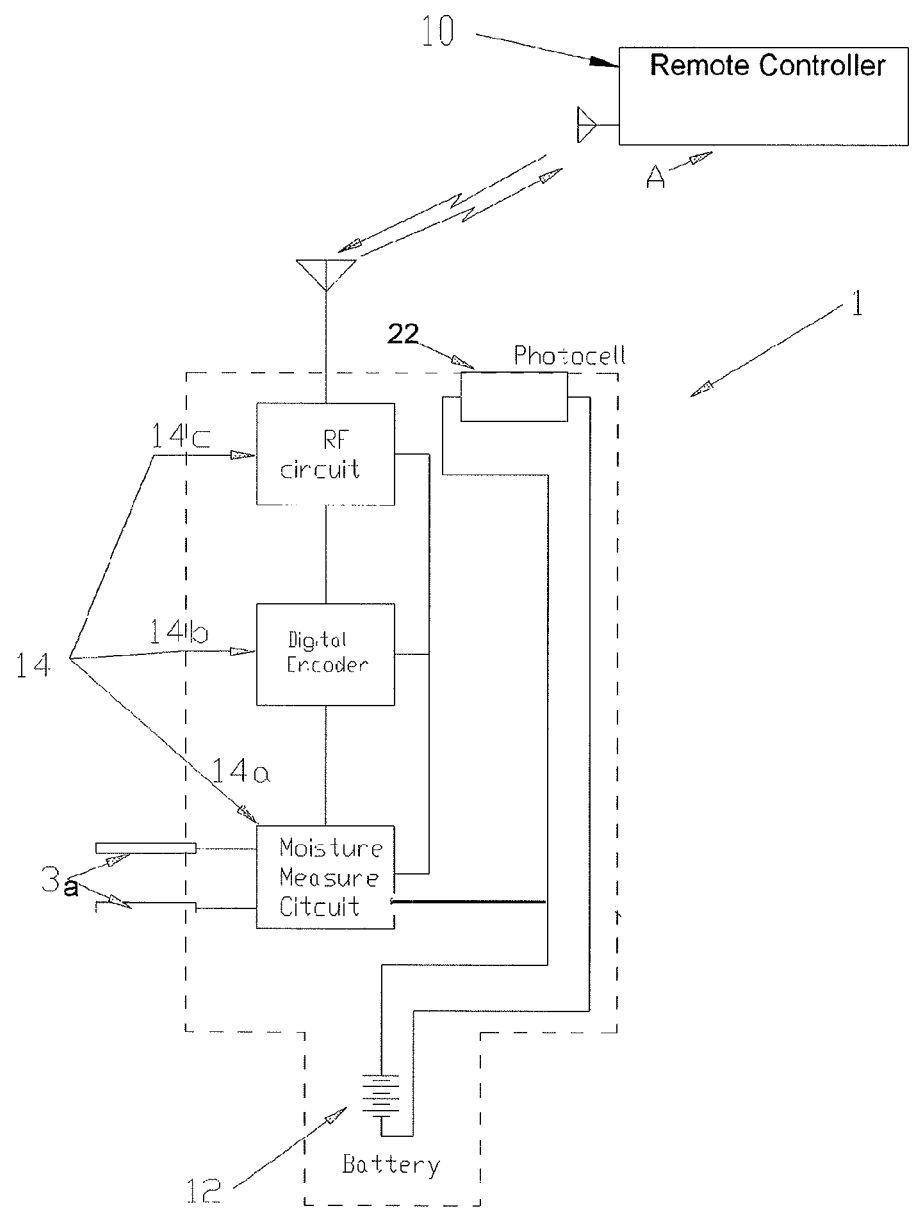
FIG. 3 is an exemplary schematic of the moisture probe of FIG. 1.

FIG. 3 illustrates an exemplary schematic diagram of the probe 1. The electrodes 3a are connected to a moisture measuring circuit 14a that provides an indication of the moisture level in the plant or tree, preferably based on capacitive impedance as noted above. More specifically, the moisture measuring circuit 14a is connected to the electrodes 3a. Preferably, one leg of an electrical bridge circuit formed by the moisture sensing circuit 14a and the electrodes 3a is energized with a 1000 Hz to 10 MHz current signal. Using higher frequencies will provide higher sensitivity of the sensor 1. A change in the imbalance across this bridge is representative of changes of moisture level surrounding the electrodes 3a. This imbalance information is preferably digitized by the digital encoder 14b and periodically transmitted by the RF circuit 14c via antenna 11. Transmission is periodic in order to minimize power usage, however, as noted above, transmission may be manually initiated via button 52. The RF circuit 14c is preferably a transceiver circuit, that is, it transmits and is capable of receiving information as well. The RF circuit 14c may receive a confirmation from the controller 10, for example, that a transmission from the probe 1 has been received. This may be used to activate the indicator 62, as noted above.

The circuit elements described above are all completely potted and molded to be totally waterproof as well. In a preferred embodiment, the battery 12 for example is rechargeable such that it need not be removed. The photocell 22 may also be used to provide power, if desired. The photocell 22 may also be used to recharge the battery, if desired. An exemplary method of determining moisture content is described in further detail in U.S. patent application Ser. No. 12/340,427, which is incorporated by reference herein.

Another approach would be to sense the power factor shift in phase between voltage and current due to the capacitance change between the electrodes 3a and the material around them and relate this to a relative number i.e. 1 through 50. If the capacitive sensing moisture electrode 3a is connected into one leg of an electrical bridge circuit, the change of electrical impedance due to high frequency will cause the bridge circuit to become more or less unbalanced and the imbalance is read as a voltage difference across opposite sides of the bridge circuit. This value is related to the moisture content of the plant material. Other suitable methods for determining moisture content of the plant, bush or tree may be used as well.

The moisture content information transmitted by the probe 1 to the controller 10 may be used in conjunction with other information, including weather reports and user programming in order to either confirm that the plant is receiving sufficient irrigation or to modify the amount of water provided in the area of the plant, bush or tree.

Figure 4:
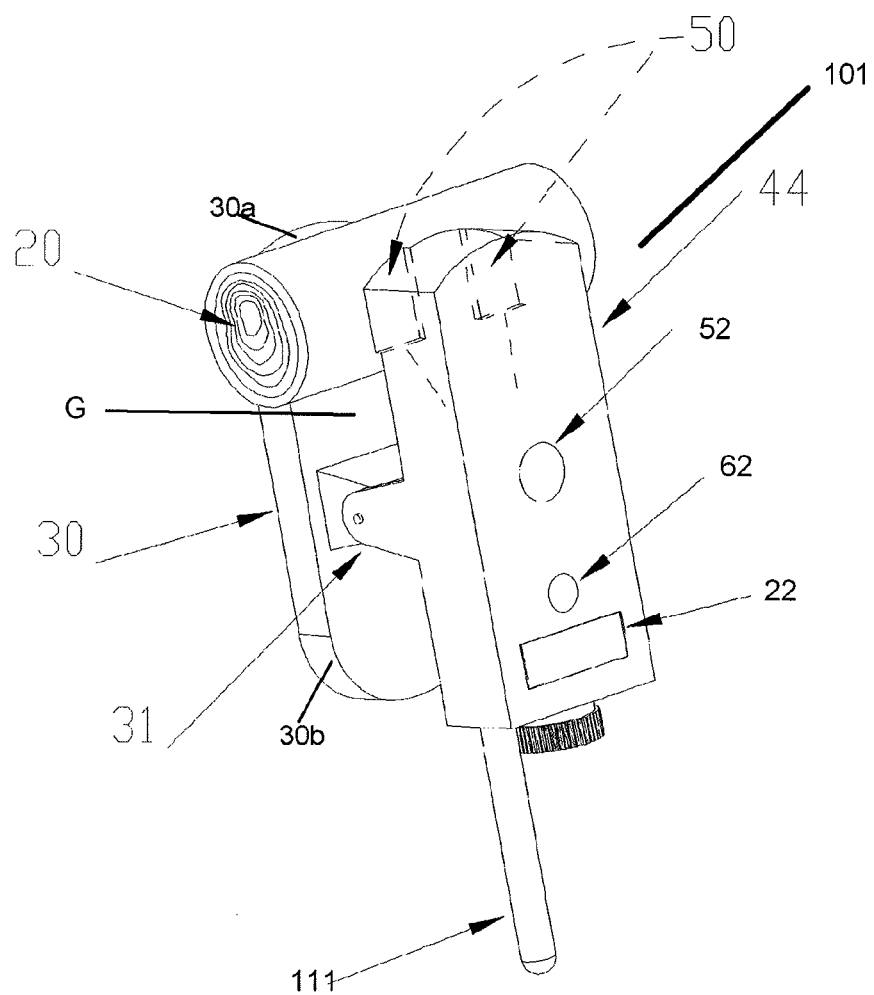
FIG. 4 illustrates a moisture probe in accordance with another embodiment of the present disclosure.

FIG. 4 illustrates another embodiment of a moisture probe or sensor 101. The probe 101 is configured for attachment to a tree limb or branch. The probe 101 includes a body 44 with a pivot arm 30 pivotally connected thereto at a pivot 31. A top end 30a of the arm 30 is biased toward the body 44 and adjacent thereto in a closed position. The top end 30a of the arm is pivotable away from the body in an open position to form a gap G when pressure is applied to the bottom end 30b thereof. A bush or tree branch or limb 20 may then be positioned in the gap G between the top portion 30a of the arm 30 and the body 44.

Figure 5:
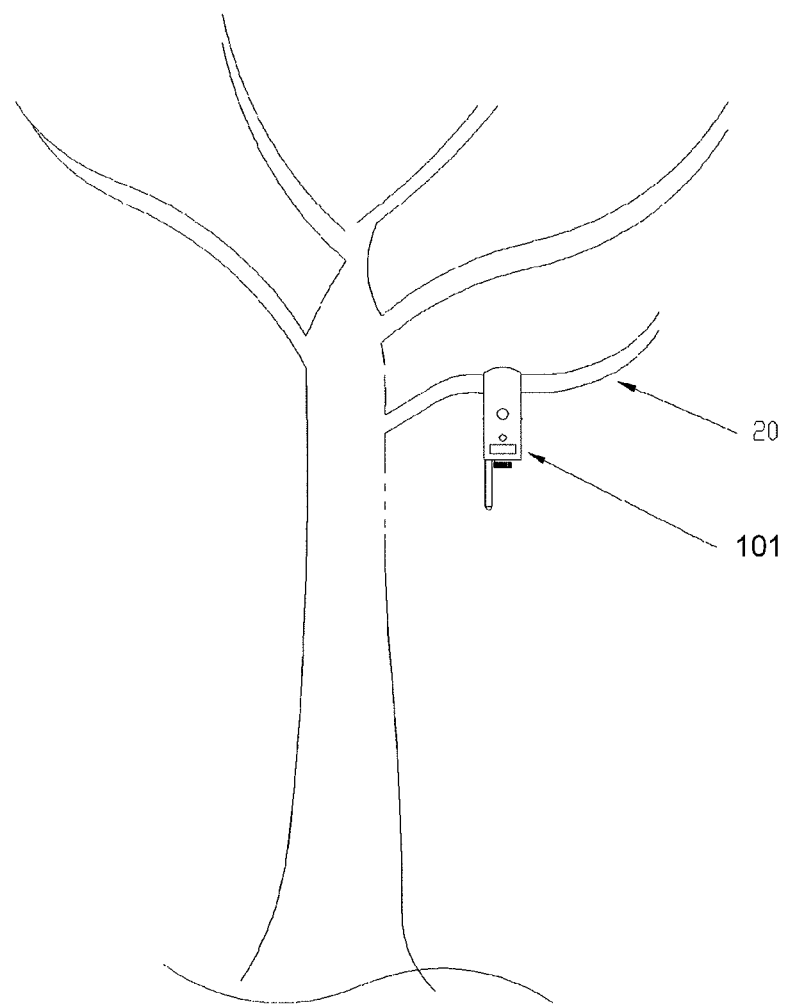
FIG. 5 illustrates the moisture probe of FIG. 4 connected to a limb of a tree.

A pair of electrodes 50 are provided on the body 44 facing the top portion 30a of the arm 30. The electrodes 50 are position to contact the tree branch or limb 20 when it is placed between the arm and the body 44, as illustrate in FIG. 4. Thus, the body 44 and arm 30 form a clip structure that allows the probe 101 to be clipped onto a tree branch or limb 20. The electrodes 50 operate in a similar manner to the electrodes 3a described above. In a preferred embodiment, as illustrated in FIG. 5, for example, the probe 101 is clipped to a limb 20 of a tree or bush.

The probe 101 includes a transmit button 52 to manually initiate transmission of moisture information to the control unit 10 and also includes the reception indicator 62 that indicates reception of the moisture information at the control unit. A photocell 22 may be provided which may be used to provide power. The probe 101 may also include a battery such as battery 12, if desired which may be rechargeable either via the photocell 22 or any other suitable device. The probe 101 preferably also includes the circuit elements 14a, 14b and 14c described above to allow for transmission of moisture information via the antenna 111.

The tree trunk and small limb moisture probe configurations shown in the FIGS. 1-5 are conceptual and drawn much larger than they need to be just for ease of seeing and describing the features. The probes 1, 101 may be configured more compactly with the sensing element only 1 cm apart, for example, and only a coin size lithium battery for example, providing power for over a year.

Although the present invention has been described in relation to particular embodiments thereof, many other variations and modifications and other uses will become apparent to those skilled in the art.

What is claimed is:

1. A moisture probe for measuring moisture content of a plant, the moisture probe comprising:
   an attachment element configured to hold two electrodes wherein the two electrodes are configured for entry into an interior of the plant;
   the attachment element including:
   a body;
   and
   measurement circuitry connected to the electrodes and operable to provide a measurement signal indicative of the moisture content in the plant based on the dielectric constant of the plant;
   wherein the measurement circuitry provides the measurement signal to provide an indication of moisture content by volume in the plant based on a dielectric constant of the plant material as sensed between the electrodes for attachment to the plant.

2. The moisture probe of claim 1, further comprising a transceiver operable to periodically transmit the measurement signal.

3. The moisture probe of claim 2, wherein the measurement circuitry and transceiver are mounted in the body.

4. The moisture probe of claim 2, further comprising a voltage source configured to provide power to the electrode, measurement circuitry and transceiver.

5. The moisture probe of claim 4, further comprising a photocell configured to provide power to the electrode, measurement circuitry and transceiver.

6. The moisture probe of claim 1, wherein the attachment element further comprises at least one pointed end configured for entry into an interior of the plant for mounting the probe.

7. The moisture probe of claim 1, wherein the plant is a bush.

8. The moisture probe of claim 1, wherein the plant is a tree.

9. A method of sensing moisture in a plant comprising:
   providing two electrodes configured for attachment to the plant;
   attaching the electrode to the plant such that the two electrodes penetrate into living material of the plant; and
   sensing, by connecting the electrodes to moisture sensing circuitry that provides an indication of moisture level based on capacitive impedance in the living material of the plant between the electrodes, and a dielectric constant of the plant material; and
   determining the moisture content by volume of the plant based on the dielectric constant of the plant material.

10. The method of claim 9, further comprising transmitting a measurement signal indicating the moisture content of the plant periodically to a control station.

11. The method of claim 10, further comprising determining health of the plant based on the moisture content.

12. A moisture probe for measuring moisture content of a plant, the moisture probe comprising:
   an attachment element configured to hold two electrodes where the electrodes are configured for entry into an interior of the plant;
   the attachment element including:
   a body;
   and
   measurement circuitry connected to the electrodes and operable to provide a measurement signal indicative of the moisture content by volume in the plant based on a dielectric constant of the plant.

* * * * *